United States Patent [19]
Nambu et al.

[11] Patent Number: 5,615,430
[45] Date of Patent: Apr. 1, 1997

[54] MEDICAL BED SYSTEM

[75] Inventors: Kyojiro Nambu; Masatoshi Tomura; Takayuki Kuwahara, all of Tochigiken, Japan

[73] Assignee: Kabushiki Kaisha Toshiba, Kawasaki, Japan

[21] Appl. No.: 518,023

[22] Filed: Aug. 22, 1995

[30] Foreign Application Priority Data

Aug. 22, 1994 [JP] Japan .................................. 6-197038
Aug. 22, 1994 [JP] Japan .................................. 6-197041

[51] Int. Cl.$^6$ .................................................. A61B 6/04
[52] U.S. Cl. ................................................ 5/600; 5/601
[58] Field of Search .............................. 5/508, 600, 601; 378/204, 205

[56] References Cited

U.S. PATENT DOCUMENTS

| | | |
|---|---|---|
| 4,584,989 | 4/1986 | Stith . |
| 4,768,241 | 9/1988 | Beney . |
| 4,879,798 | 11/1989 | Petre . |
| 5,072,906 | 12/1991 | Foster . |
| 5,077,843 | 1/1992 | Dale et al. . |

FOREIGN PATENT DOCUMENTS 64-52436   2/1989   Japan .

OTHER PUBLICATIONS

Int. J. Radation Oncology Biol. Phys., vol. 14. pp. 373–381; A System For Stereotactic Radiosurgery With A Linear Accelerator; Wendell Lutz, PH.D et al.
Int. J. Radation Oncology Biol. Phys., vol. 14. pp. 115–126; Dynamic Stereotactic Radiosurgery; Ervin B. Podgorsak, PH.D., FCCPM et al.
The Defense Medical Academy, p. 87, Apr. 13–16, 1995, Akira Shioda, et al., "Radiosurgery Using Single Couch Treatment Unit", (with English translation), Japan.
Int. J. Radiation Oncology, Biology, Physics, vol. 11, No. 6, Jun. 1995, G. H. Hartmann, et al., "Cerebral Radiation Surgery Using Moving Field Irradiation At A Linear Accelerator Facility".

*Primary Examiner*—Bentsu Ro
*Attorney, Agent, or Firm*—Oblon, Spivak, McClelland, Maier & Neustadt, P.C.

[57] ABSTRACT

A medical bed system, is provided wherein, by enabling a plurality of medical apparatus to use a common bed, various medical activities can be taken without moving a patient to another bed and thus without changing an attitude of the patient. In particular, the medical bed system includes a rotating section for rotating the bed horizontally around a predetermined central axis to position it on predetermined locations of the medical apparatuses, and an engaging section for engaging selectively the bed with each of the medical apparatuses, whereby positioning precision of the bed can be improved. In addition, each of a plurality of medical apparatuses can generate own bed operation control signal for operating the bed to fit to own medical apparatus, and can supply own bed operation control signal to the bed when it is engaged with the bed by the engaging section, and the bed can control its operation based on the bed operation control signal supplied from each of the plurality of medical apparatuses, whereby timing synchronization between the bed and the medical apparatus is achieved automatically.

12 Claims, 12 Drawing Sheets

MEDICAL BED SYSTEM

BACKGROUND OF THE INVENTION

1. Field of the Invention

The present invention relates to a medical bed system wherein one bed is shared in a plurality of medical apparatuses such as an X-ray CT apparatus, radiotherapeutical apparatus, and the like.

2. Description of the Prior Art

Recently, radiotherapy in which narrow radiation beams are concentrated to an endocardial lesion so as to destroy only this lesion has been tried. This technology is described in the two theses of "A SYSTEM FOR STEREOTACTIC RADIOSURGERY WITH A LINEAR ACCELERATOR" by WENDELL LUTS, Ph.D. et al in Int. J. Radiation Oncology Biol. Phys. Vol.14 pp.373–381 and "DYNAMIC STEREOTACTIC RADIO SURGERY" by ERVIN B. PODGORSAK, Ph.D. et al in the same journal pp.115–126. In this case, this radiotherapy must be conducted to exert no influence upon normal cells around the lesion. In some cases, the radiotherapy has also been conducted over several weeks. In this case, a reproducibility capable of concentrating the narrow radiation beams to the same spot of the lesion every time must be maintained. On the other hand, location of the lesion can be specified at present by the X-ray CT apparatus with precision of about ±1 mm or less.

In the meanwhile, in an ordinary case, the radiotherapeutical apparatus, a therapy positioning apparatus (simulator) and the X-ray CT apparatus are used together upon conducting a radiotherapy treatment. However, ordinarily these apparatuses are respectively installed in different rooms. Therefore, upon treating the lesion, a patient as the subject must be moved between respective apparatuses. Consequently, much time and labor have been required and, in addition, sufficient positioning precision could not be attained.

As a result, a system has been considered wherein one bed on which the patient lies is commonly used in a plurality of therapeutical apparatuses such as the X-ray CT apparatus, a linear accelerator, etc. One example is shown in the publication of Japanese patent publication No.64-52436.

However, in a system using one bed commonly to the X-ray CT apparatus and the linear accelerator, for example, it is required that a location of an isocenter of the X-ray CT apparatus and a location of an isocenter of the linear accelerator must be switched mutually with precision when, for example, the direction of the bed should be changed. Nevertheless, at present, the location of tile isocenter is indicated by a light beam emitted from a laser beam projector, etc. and the apparatus is then positioned to the isocenter manually and mechanically. As a result, they cannot be accurately positioned.

On the other hand, the bed apparatus in this system is equipped with a control apparatus which comprises, for example, a CPU, and a memory for storing an operation control program for the X-ray CT apparatus and an operation control program for the radiotherapeutical apparatus, etc. When the X-ray CT apparatus is used, it is controlled by the operation program therefor. Also when the radiotherapeutical apparatus is used, it is controlled by the operation program therefor.

But, to control the X-ray CT apparatus and the radiotherapeutical apparatus by one control apparatus, a control software becomes complicated. Further, the X-ray CT apparatus and the radiotherapeutical apparatus are switched manually, and synchronizing timings of operations between the X-ray CT apparatus and the radiotherapeutical apparatus are manually handled. As a result, plenty of time and labor are required.

In addition, the movements of the beds of those apparatus are different from each other. For example, the bed can be rotated around the isocenter of the linear accelerator, but the X-ray CT apparatus does not equip the control function for driving the bed around the isocenter of the CT apparatus. Also, the X-ray simulator does not equip the function for rotating the bed around the isocenter.

SUMMARY OF THE INVENTION

The present invention has been made in view of the above circumstances, and an object of the present invention is to provide a medical bed system capable of performing radiotherapy etc. with precision and effectively.

Another object of the present invention is to provide a medical bed system capable of eliminating a particular software for controlling its operation to share one bed, and synchronizing automatically operational timing between a switching operation of a system main body to use the bed and an operation of the bed.

In order to achieve the above objects, according to the present invention, there is provided a medical bed system comprising a bed on which a subject lies, a plurality of medical apparatuses sharing said bed, and engaging means for engaging said bed with each of said plurality of medical apparatuses.

In addition, the present invention provides a medical bed system further comprising means for rotating said bed horizontally around a predetermined central axis so as to position said bed on a predetermined location of respective medical apparatuses.

According to the above configurations, various medical activities can be taken without moving the patient from a bed to another bed and thus without changing an attitude of the patient, and positioning precision of the bed can be improved.

In a preferred embodiment of the present invention, said rotating means includes a swing arm to be rotated around a predetermined central axis and a turn table rotatably mounted on said swing arm, and each of said plurality of medical apparatuses is arranged such that respective isocenters of said plurality of medical apparatuses are put on a locus of a central axis of said turn table.

According to the above embodiment, since isocenters can coincide with each other only by adjusting a rotation angle of a swing arm, positioning of the bed becomes relatively easy, and thus its mechanical precision can be readily maintained.

The present invention provides a medical bed system comprising a bed on which a subject lies a plurality of medical apparatuses sharing said bed wherein each of said plurality of medical apparatuses can generate its own bed operation control signal for operating said bed to fit to its own medical apparatus, and can supply said own bed operation control signal to said bed when it occupies said bed, and said bed can control its operation based on said bed operation control signal supplied from each of said plurality of medical apparatuses.

According to the above configuration, it is not necessary for the bed per se to be equipped with a particular software for controlling an operation of the bed, and synchronization of operation timing between the bed and the medical apparatus can be taken automatically.

In addition, the present invention provides a medical bed system further comprising engaging means for engaging said bed with each of said plurality of medical apparatuses, wherein each of said plurality of medical apparatuses can supply said own bed operation control signal to said bed when it is engaged with said bed by said engaging means.

In another preferred embodiment of the present invention, each of said plurality of medical apparatuses includes means for detecting its own engagement with said bed, and said bed includes means for switching signal lines such that, in response to an output signal of said detecting means, said bed operation control signal is input into said bed from a corresponding one of said plurality of medical apparatuses.

In still another preferred embodiment of the present invention, said engaging means includes a pair of contact members to which signal lines for supplying said bed operation control signal are connected, and, when said bed is engaged with a corresponding one of said plurality of medical apparatuses, both of said pair of contact members are contacted so as to supply said bed operation control signal from a said corresponding one of said plurality of medical apparatuses to said bed.

DESCRIPTION OF THE PREFERRED EMBODIMENTS

There will now be described preferred embodiments of the present invention hereinafter with reference to the accompanying drawings.

Figure 1:
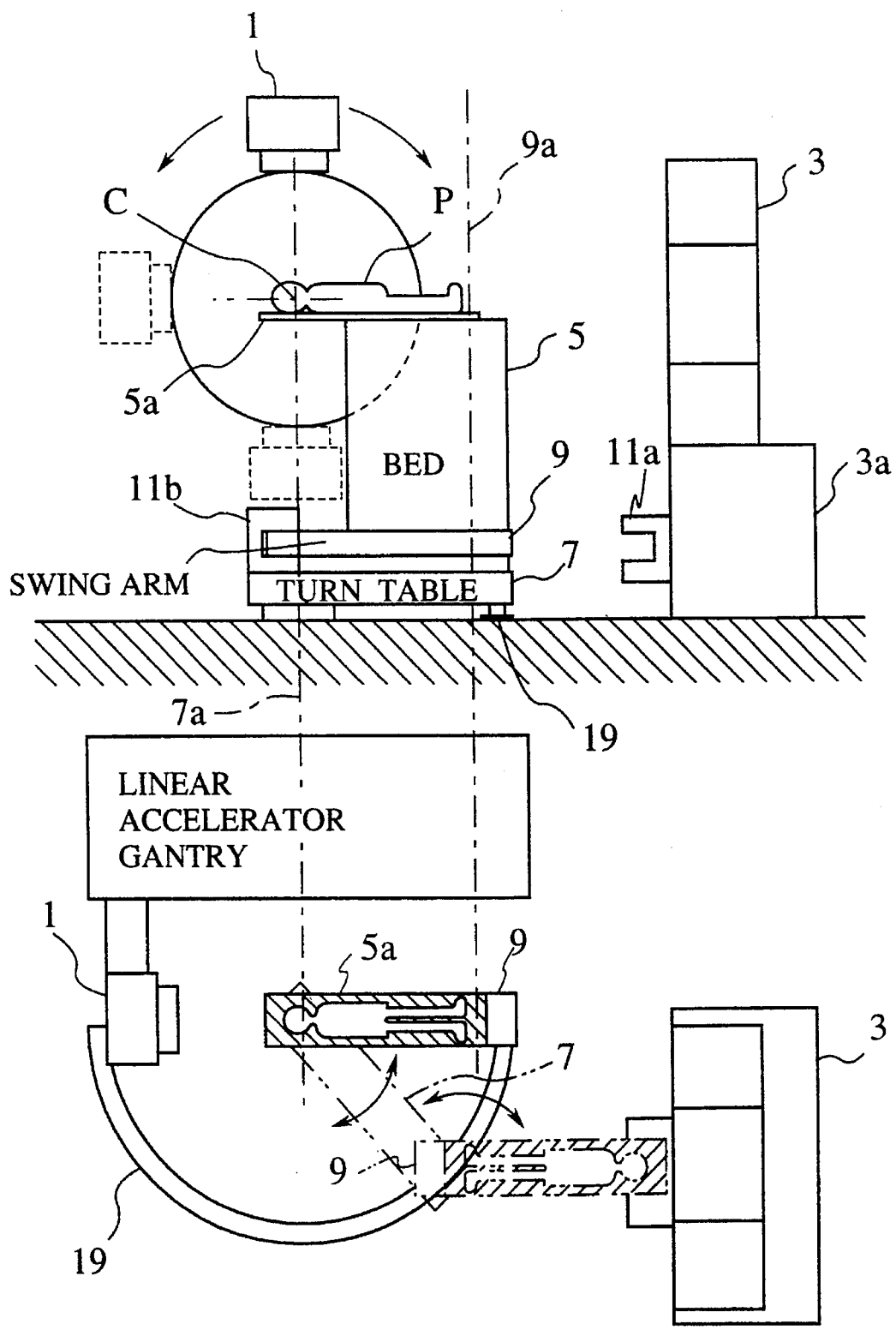
FIG. 1 is a schematic view showing a configuration of a medical bed system according to a first embodiment of the present invention.

FIG. 1 is a schematic view showing a configuration of a medical bed system according to a first embodiment of the present invention. In FIG. 1, an upper portion thereof is a front view, and a lower portion thereof is a plan view.

A linear accelerator 1 is so formed rotatably that it can be rotated around a concerned part of a subject P as a center. Thus, if the linear accelerator 1 is rotated in an arbitrary direction, a radiation (radiant ray) can be irradiated to the concerned part of the subject P. An X-ray CT apparatus 3 is positioned on a predetermined location near the linear accelerator 1, described later. The X-ray CT apparatus 3 is equipped on a predetermined location with a hook mechanism 11a, which is formed to direct to a bed 5.

The bed 5 is placed between the linear accelerator 1 and the X-ray CT apparatus 3. In the bed 5, a tabletop 5a on which the subject P lies may be formed vertically movably and also back and forth movably in the direction of a body axis of the patient P.

Further, the bed 5 is mounted on a swing arm 9 and a turn table 7 so as to move the tabletop 5a to a predetermined location. Another hook mechanism 11b is provided on the turn table 7.

With holding the tabletop 5a substantially horizontally, the turn table 7 can be rotated along a rail 19 within a range of 180°. The rail 19 is laid down along a semicircle which has a rotation axis 7a of the turn table 7 as a center. While keeping the tabletop 5a substantially horizontally, the swing arm 9 can be rotated 360° around its rotation axis, i.e., its rotation axis 9a of the swing arm 9, which is located movably near the semicircle of the turn table 7 (substantial location of the rail 19). A plate 21 which must be engaged with the hook mechanism 11 (see FIGS. 3 to 5) is provided at the top portion of the swing arm 9. Incidentally, the hook mechanism 11b provided on the bed 5 is the same as the hook mechanism 11a provided on the X-ray CT apparatus 3, as described in advance.

Figure 2:
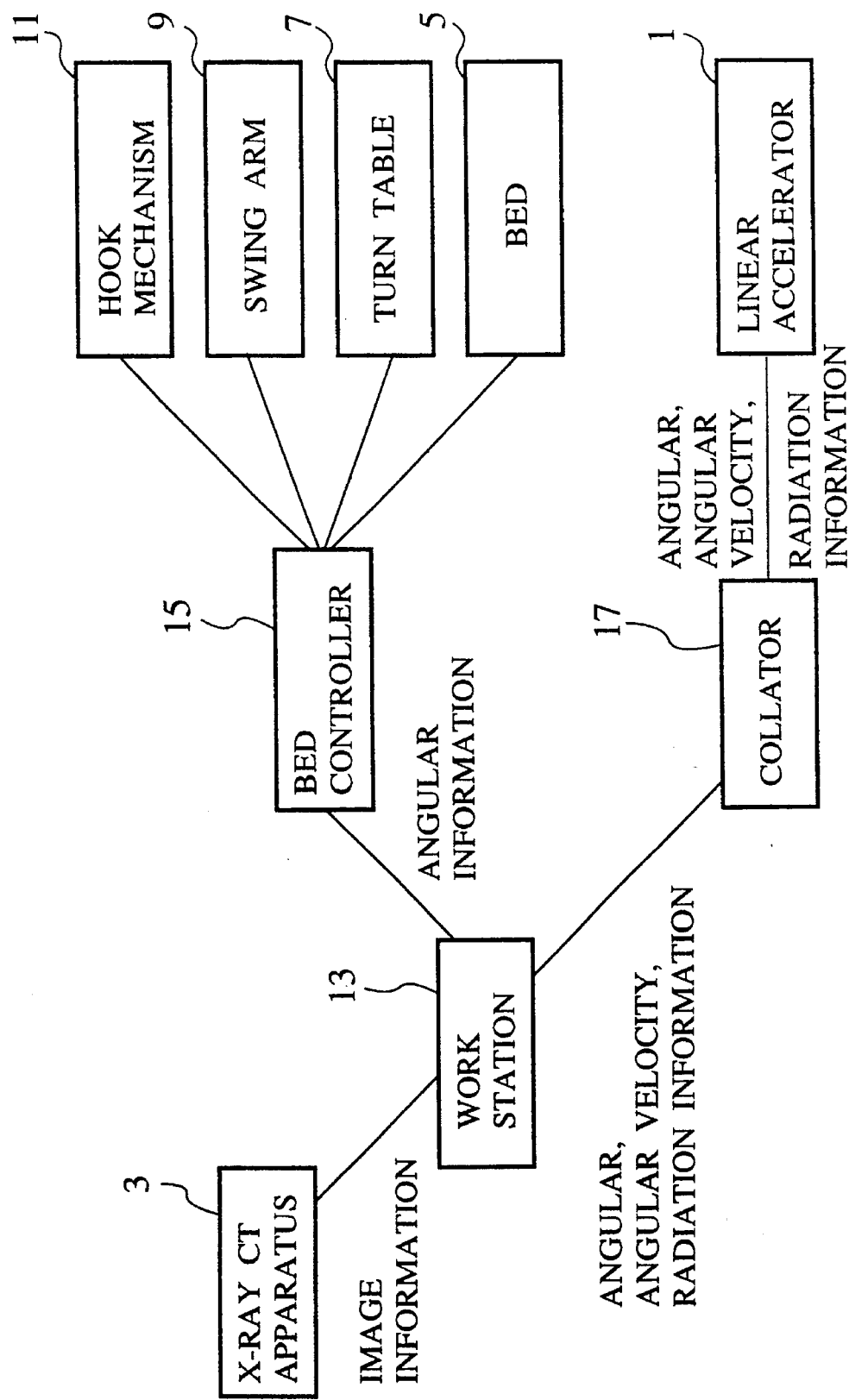
FIG. 2 is a block diagram showing a configuration of the medical bed system in FIG. 1.

FIG. 2 is a block diagram showing a configuration of the medical bed system according to the first embodiment of the present invention.

As shown in FIG. 2, the linear accelerator 1 and the X-ray CT apparatus 3 are connected to each other via a work station 13 and a collator 17. A bed controller 15 is connected to the work station 13. The bed 5, the turn table 7, the swing arm 9, and the hook mechanism 11a, 11b, all being controlled by the bed controller 15, are connected to the bed controller 15.

In the configuration shown in FIGS. 1 and 2, when the radiotherapy is conducted to the patient by the linear accelerator 1, a plate 21 of the swing arm 9 is fixed to the hook mechanism 11 on the turn table 7. Further, the patient is treated while the bed 5 is rotated along the rail 19 around the central axis 7a of the turn table 7 as a center if required. On the contrary, when the patient is diagnosed by the X-ray CT apparatus 3, the bed 5 is rotated around the central axis 9a of the swing arm 9 as a central axis. Then, the plate 21 provided at the top of the swing arm 9 is fixed to the hook mechanism 11 provided on the X-ray CT apparatus 3. Diagnoses are performed while the tabletop 5a is slid if necessary.

Figure 3A:
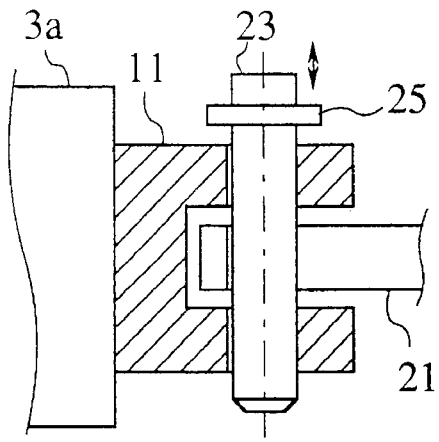
FIGS. 3A to 3C are partially sectioned side views, each illustrating an embodiment of a plate and a hook mechanism of the medical bed system in FIG. 1.
Figure 3B:
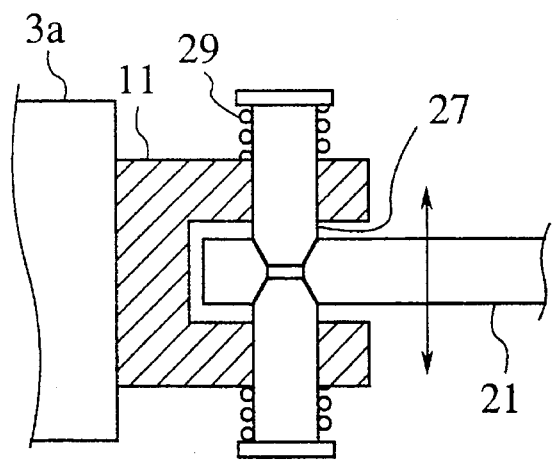
Figure 3C:
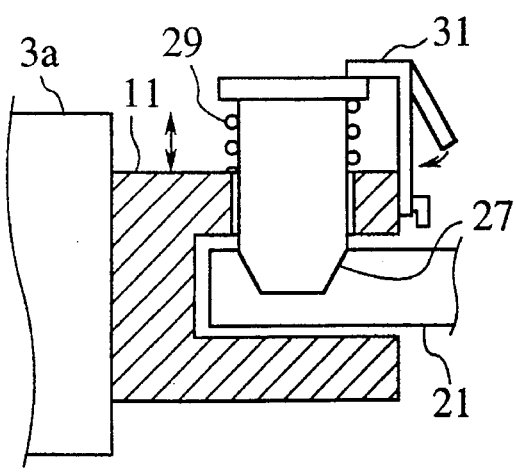

FIGS. 3A to 3C are views showing several embodiments of fixing methods by a plate 21 and a hook mechanism 11. In FIG. 3A, the hook mechanism 11 and the plate 21 are engaged by passing a shaft 23 into holes provided in the hook mechanism 11 and the plate 21 and then fitting a disconnection preventing pin 25 into a hole of the shaft 23. In FIG. 3B, the hook mechanism 11 and the plate 21 are engaged by piercing tapered holes in the plate 21 from both front and back surfaces of the plate 21 and then abutting tapered top portions of tapered pins 27 against the tapered holes from both upward and downward directions, and then pressing the tapered pins 27 to the plate 21 by springs 29. In this case, a slight displacement between the bed and the medical apparatus can be overcome by tapered portions, and a position of the bed can also be fixed by the tapered portions in a vertical direction. Further, so not to prevent an engagement between the hook mechanism 11 and the plate 21, these tapered pins 27 can be separated electromagnetically or hydraulically in the vertical direction when the plate 21 is inserted into the hook mechanism 11. In FIG. 3C, the hook mechanism 11 and the plate 21 are engaged and fixed by employing a tapered pin 27, a spring 29 and a punch key 31.

In the above explanations, the hook mechanism 11 has been provided on the X-ray CT apparatus 3 whereas the plate 3 has been provided on the swing arm 9. However, on the contrary, the hook mechanism 11 may be provided on the swing arm 9 while the plate 21 may be provided on the X-ray CT apparatus 3. In the contrary case, since the plate of which structure is simple, is attached to each of the plural apparatus such as X-ray apparatus, it becomes more easy to produce.

Next, in case one bed is commonly used by a plurality of medical apparatuses, a method of controlling an operation of the bed will be explained.

Figure 4:
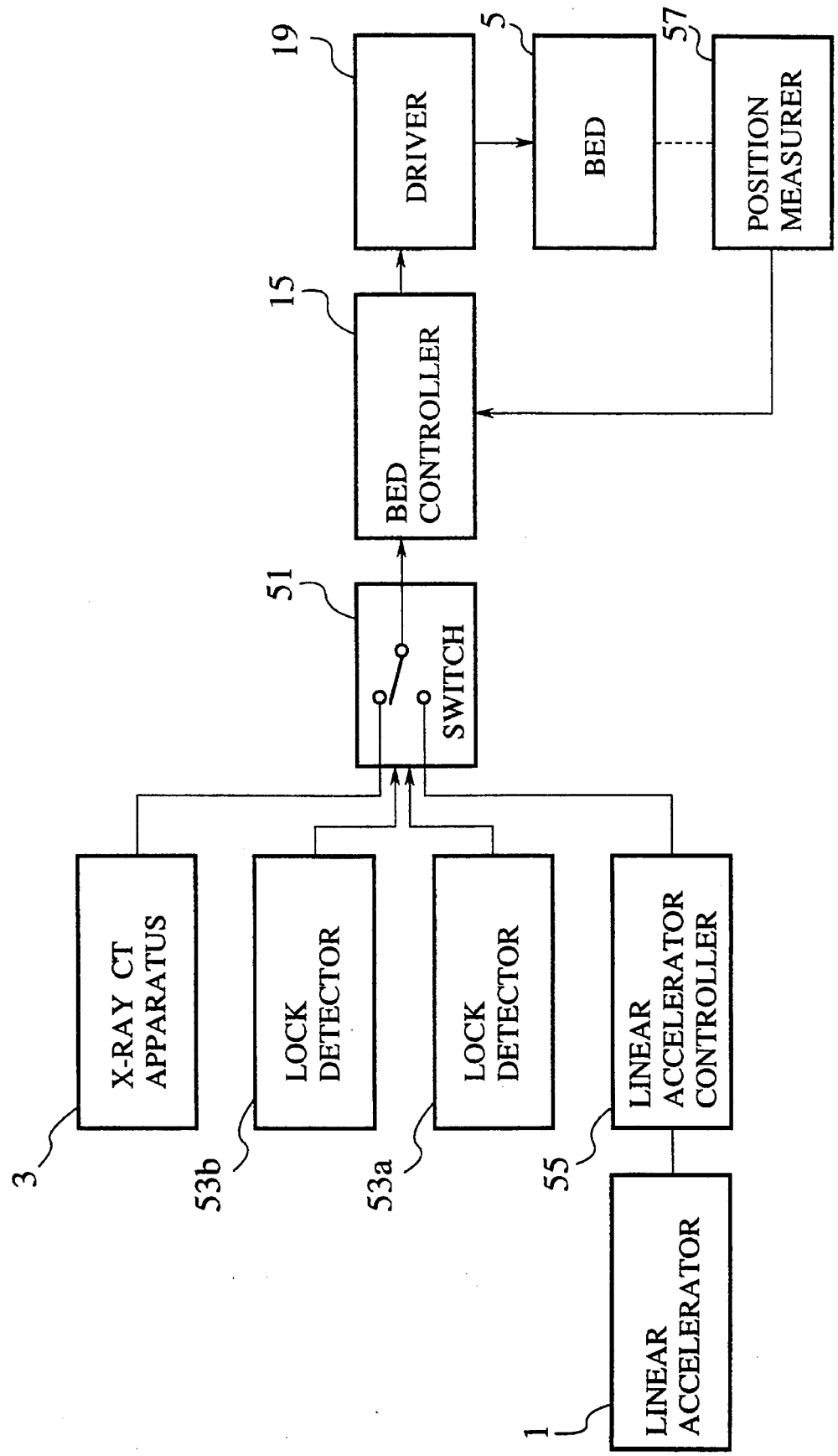
FIG. 4 is a block diagram showing an example of a method of controlling an operation of the bed.

FIG. 4 is a block diagram showing an example of a method of controlling an operation of the bed. In the method shown in FIG. 4, there are provided a lock detector 53a for detecting whether or not the bed 5 is connected to the linear accelerator 1, and a lock detector 53b for detecting whether or not the bed 5 is connected to the X-ray CT apparatus 3. In other words, if the lock detector 53a detects the connection, it supplies a signal informing this connection to a switch 51. Based on this signal, the switch 51 connects a linear accelerator controller 55 to a bed controller 15. Therefore, in this case, the bed controller 15 controls the bed 5 based on a control signal supplied from the linear accelerator controller 55. On the other hand, if the lock detector 53b detects the connection, it supplies a signal informing this connection to a switch 51. Based on this signal, the switch 51 connects the X-ray CT apparatus 3 to the bed controller 15. Thus, in this case, the bed controller 15 controls the bed 5 based on a control signal supplied from the X-ray CT apparatus 3. In accordance with location information of the bed 5 derived from a position measurer 57, the bed controller 15 executes a feedback control so as to place the bed 5 on a desired location.

Subsequently, detailed examples of lock detectors 53a, 53b will be explained.

Figure 5:
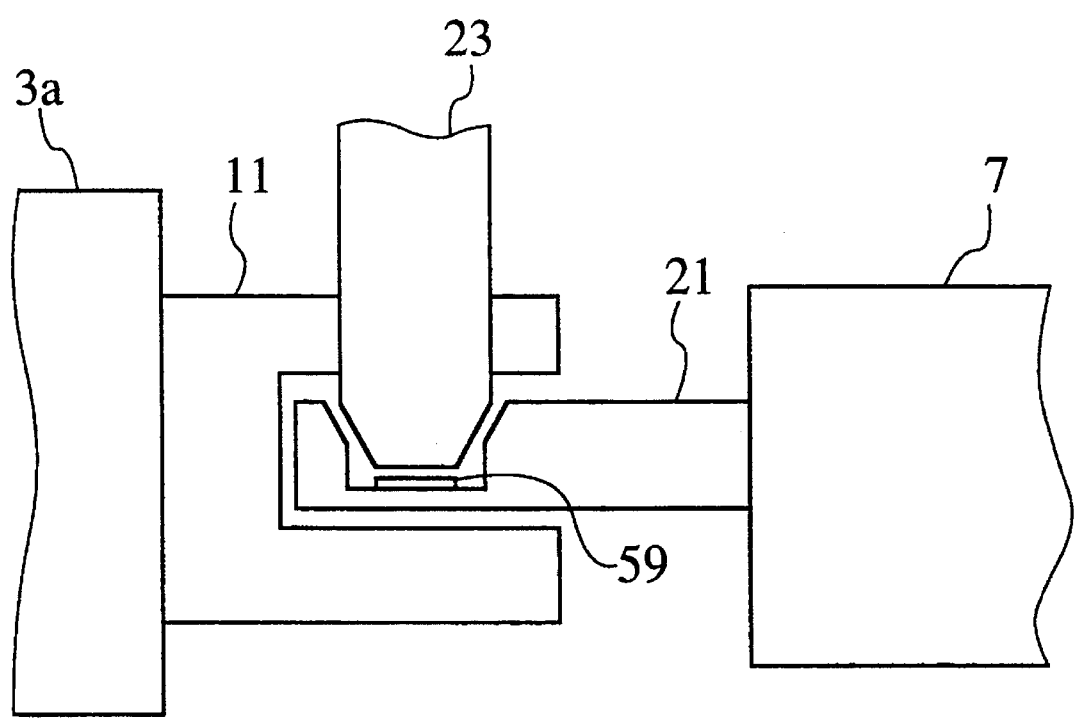
FIG. 5 is a side view illustrating an example of lock detectors.

FIG. 5 is a side view illustrating an example of lock detectors 53a, 53b. For example, in the fixing method formed of the plate 21 and the hook mechanism 11 as shown in FIG. 3C, a limit switch 59 may be used, as shown in FIG. 5. The lock detectors 53a, 53b are not limited to this example. Various methods such as a mechanical method, electrical method, and optical method may be considered.

Here, an operation of the medical bed system of the present invention will be explained in detail according to this configuration.

First, in case the bed 5 is placed on a predetermined location of the linear accelerator 1, the lock detector 53b detects the bed 5 to output a detection signal to the switch 51. Based on a detection signal output from the lock detector 53a, the switch 51 switches the control such that an operation of the bed 5 is controlled by the linear accelerator 55 of the linear accelerator 1. Thereby, control signals including operation control programs corresponding to operations such as "PLACE TABLETOP OF BED 5 ON DESIGNATED LOCATION", and "SET ROTATION ANGLE OF BED FROM ISOCENTER (RADIATION CENTER) TO DESIGNATED VALUE", for example, are output from the linear accelerator controller 55. The control signals are supplied to the bed controller 15 via the switch 51. A driver 19 operates the bed 5 according to the control signals.

In addition, control signals including operation control programs corresponding to operations such as "MOVE BED 5 TOWARD X-RAY CT APPARATUS 3" etc. After the bed 5 is moved to a desired location of the X-ray CT apparatus 3, the lock detector 53b detects such movement of the bed 5 and outputs a detection signal to the switch 51.

In accordance with the detection signal output from the lock detector 53b, the switch 51 may switch the control such that an operation of the bed 5 is controlled by a bed control apparatus of the X-ray CT apparatus 3. As a result, control signals including operation control programs corresponding to operations such as "EXECUTE PULL-OUT OPERATION OF TABLETOP OF BED 5 IN LONGITUDINAL DIRECTION AT RATE OF xx CM/SEC for xx SECONDS", "SET HEIGHT OF TABLETOP OF BED 5 TO DESIGNATED VALUE", etc. are output from the bed control apparatus of the X-ray CT apparatus 3. The control signals are supplied to the bed controller 15 via the switch 51. The driver 19 operates the bed 5 based on the control signals.

Figure 6:
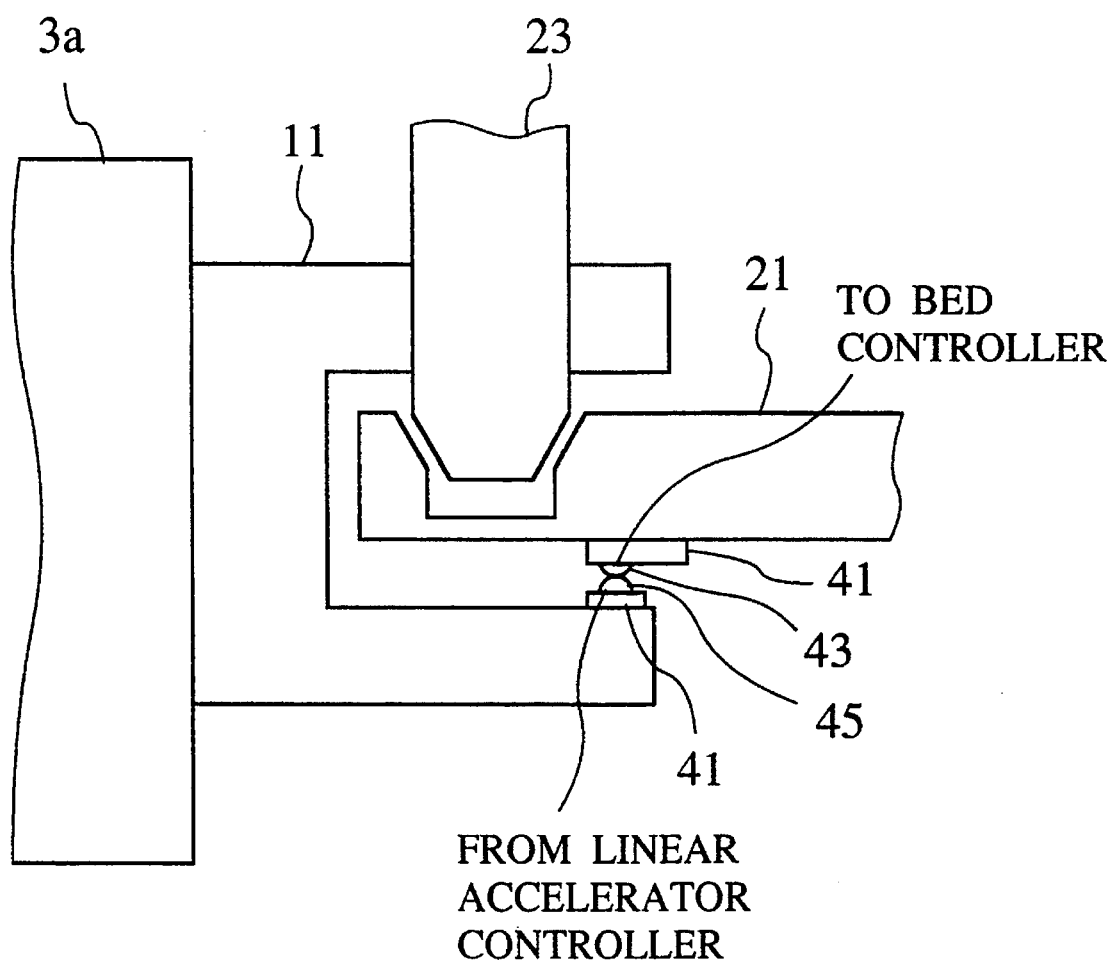
FIG. 6 is a side view illustrating another example of the method of controlling the operation of the bed.

FIG. 6 is a side view illustrating another example of the method of controlling the operation of the bed. In the above embodiment, control signal lines are extracted from both of the linear accelerator 1 and the X-ray CT apparatus 3 into the bed 5, and the control signal lines are switched by the switch 51 in response to the signal from the lock detector 53 so as to be connected to a suitable control signal supply source. However, in the embodiment shown in FIG. 6, control signal lines are extracted into the hook mechanism 11 and the plate 21 per se and contact points are provided thereon. In other words, a bed side contact 43 is provided on a predetermined portion of the plate 21 via an insulating material 41. Also, a medical apparatus side contact 45a (45b) is provided on a predetermined portion of the hook mechanism 11 in the linear accelerator 1 (the X-ray CT apparatus 3) via an insulating material 41. Therefore, the plate 21 and the hook mechanism 11 are fixed on predetermined locations. At the same time, the bed side contact 43 and the medical apparatus side contact 45 are contacted. The control signals are transmitted via the contact. According to this method, means for determining a particular medical apparatus to which the contacts have been connected can be neglected. In addition, the contact method is not restricted to the electrical contacts, but other signal connecting methods such as an optical method may be utilized.

Figure 7:
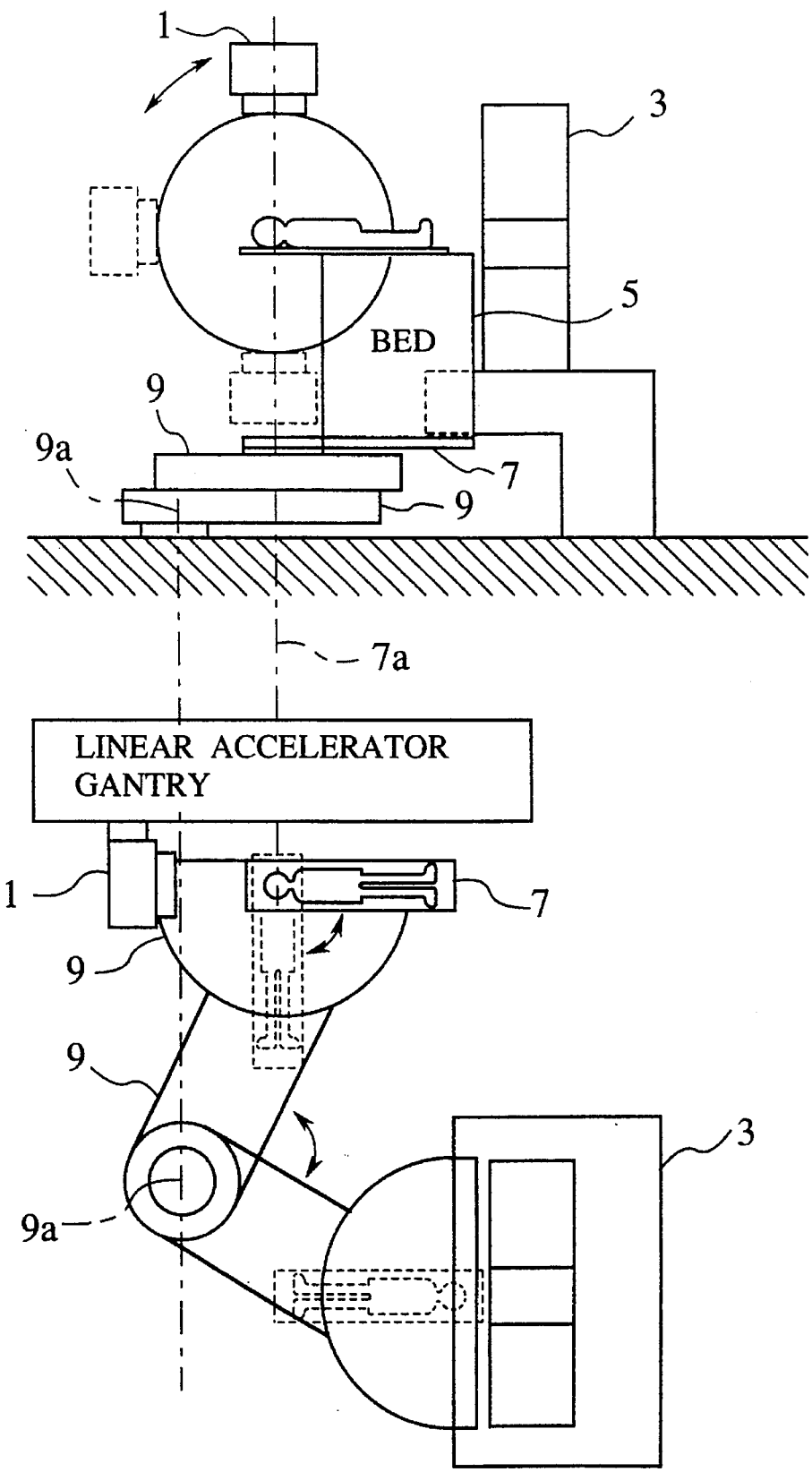
FIG. 7 is a schematic view showing a configuration of a medical bed system according to a second embodiment of the present invention.

FIG. 7 is a schematic view showing a configuration of a medical bed system according to a second embodiment of the present invention. In FIG. 7, an upper portion thereof is a front view and a lower portion thereof is a plan view. In this second embodiment, a central axis 9a of the swing arm 9 is fixed. Then, isocenters, scancenters, etc. of respective medical apparatuses are put on a locus of the central axis 7a of the turntable 7 when the swing arm 9 is turned around this axis as a central axis.

Figure 8:
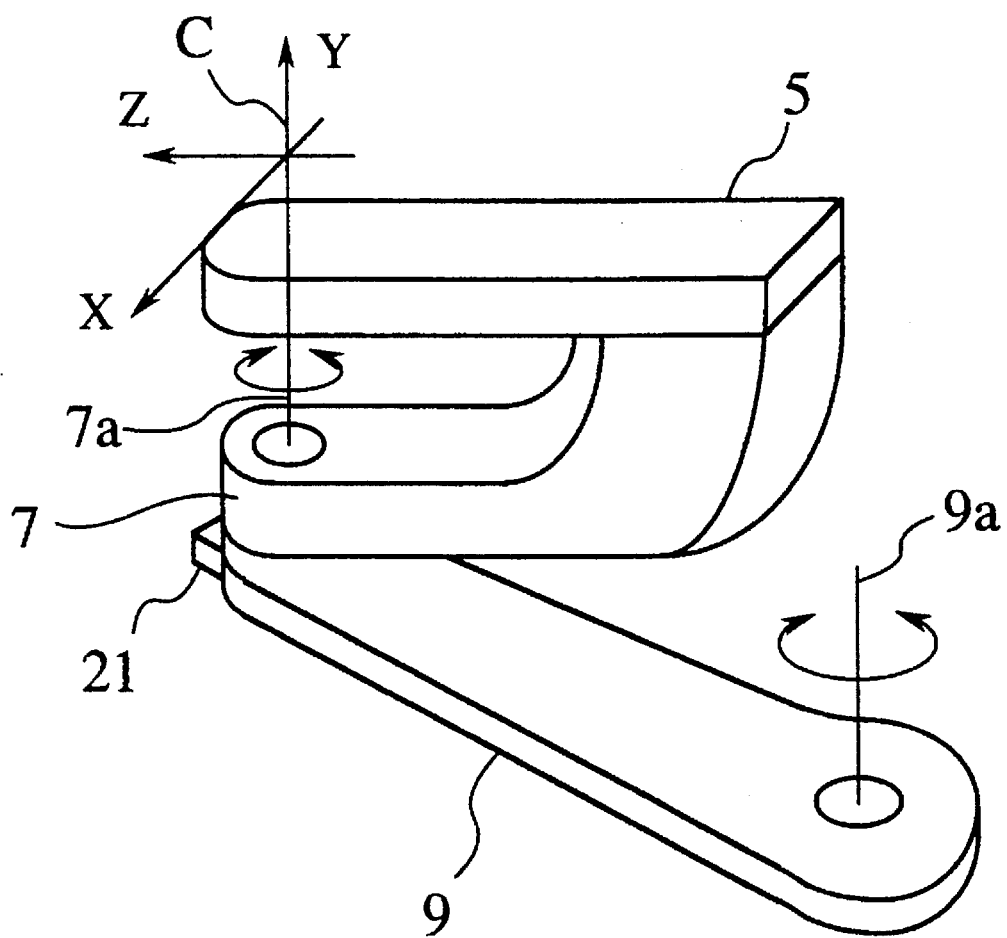
FIG. 8 is a perspective view showing a relationship of central axes of a turn table and a swing arm in FIG. 7.
Figure 9:
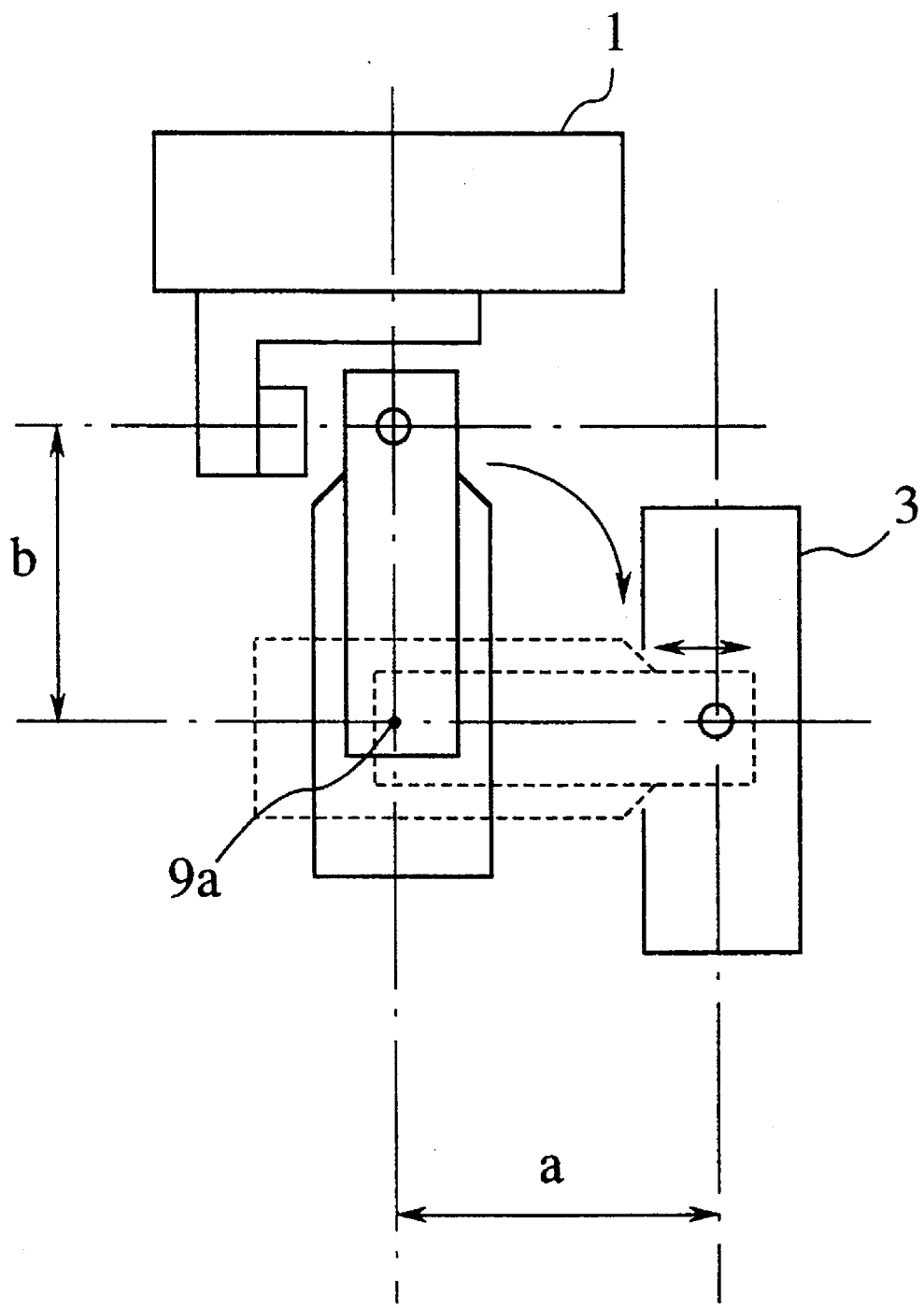
FIG. 9 is a plan view showing a distance relationship around the central axis of the swing arm in FIG. 7.

FIG. 8 is a perspective view showing a relationship of a central axis 7a of the turn table 7 and a central axis 9a of the swing arm 9 in the second embodiment of FIG. 7. In the second embodiment, the swing arm 9 is so constituted that it can be rotated around the fixed central axis 9a of the swing arm 9. The turn table 7 is rotatably mounted at the other end of the swing arm 9, and the bed 5 can be rotated when the turn table 7 is rotate about the central axis 7a of the turn table 7. Further, the plate 21 for fixing the swing arm 9 to respective medical apparatuses is provided on an end portion, where the turn table 7 is mounted, of the swing arm 9. Furthermore, in this second embodiment, as shown in FIG. 9, a distance a between a scan center of the X-ray CT apparatus 3 and the central axis 9a of the swing arm 9 is set to be equal to a distance b between the isocenter of the linear accelerator 1 and the central axis 9a of the swing arm 9.

Subsequently, a detailed operation of the second embodiment of the present invention will be explained. Assume that the bed 5 shared by the linear accelerator 1 and the X-ray CT apparatus 3 is at first placed on the X-ray CT apparatus 3 and then moved toward the linear accelerator 1. First, in order to prevent contact between the tabletop 5a and the X-ray CT apparatus 3, the tabletop 5a of the bed 5 is retracted. Then, an engagement between the hook mechanism 11 of the X-ray CT apparatus 3 and the plate 21 of the swing arm 9 is released. Next, the bed 5 is placed by rotating the swing arm 9 on the linear accelerator 1 so that the hook mechanism 11 of the linear accelerator 1 and the plate 21 of the swing arm 9 are engaged with each other. Finally, the tabletop 5a of the bed 5 is expanded to be restored to its original location. When the bed 5 is placed on the X-ray CT apparatus 3, the angle of the turn table 7 is fixed so as to prevent contact between the tabletop 5a and the X-ray CT apparatus 3.

With the above, although two medical apparatuses have been discussed as an instance, this second embodiment may be applied to three medical apparatuses or more.

Figure 10:
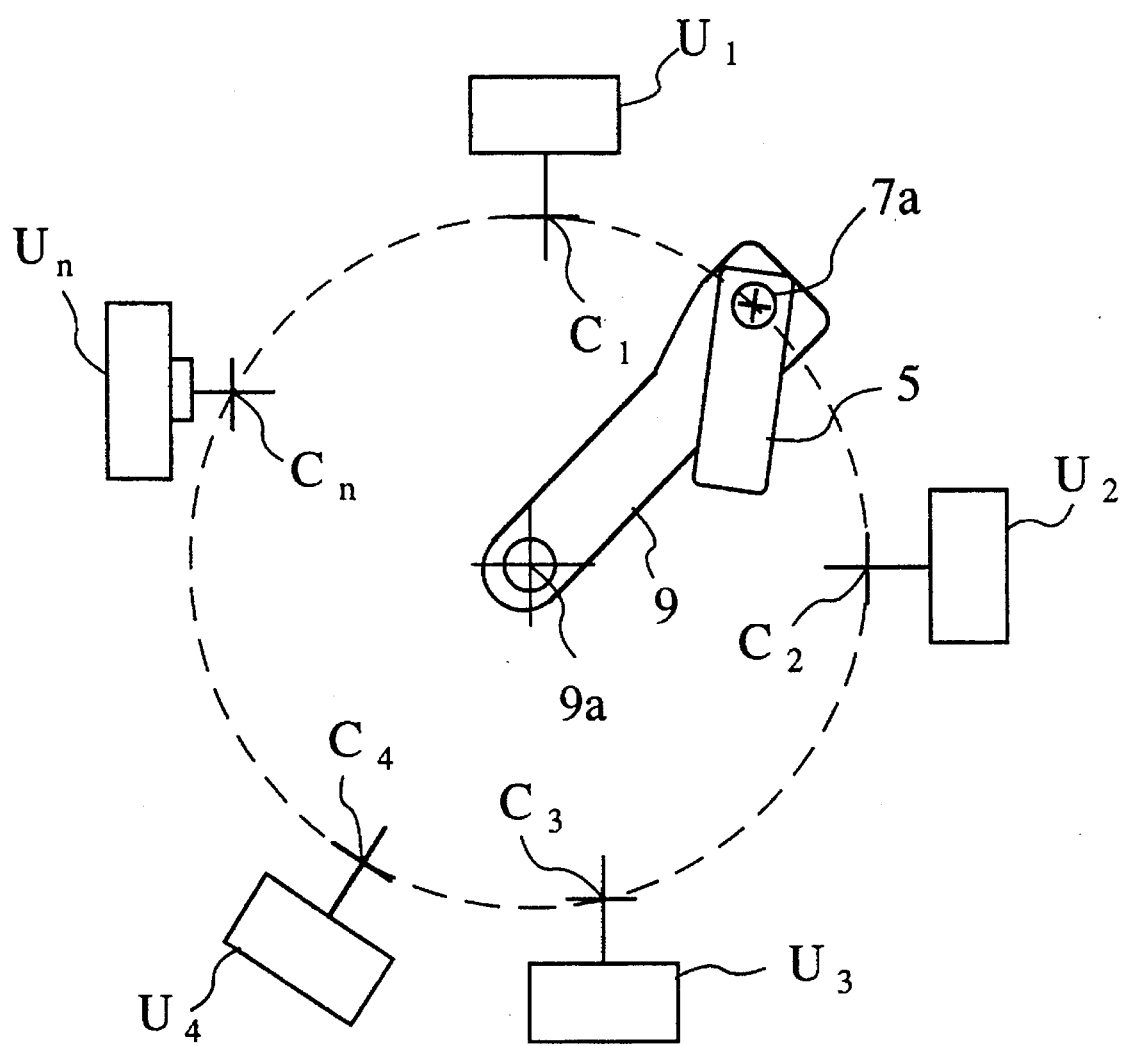
FIG. 10 is a plan view showing a case wherein the present invention is applied to three medical apparatuses or more.

FIG. 10 is a plan view showing a case wherein the present invention is applied to three medical apparatuses or more. In FIG. 10, all isocenters C1, C2, . . . , Cn of a plurality of medical apparatuses U1, U2, . . . , Un are put on the same concentric circle. More particularly, in case a plurality of the linear accelerators 1 are arranged, all isocenters are put on the same circle. In case the X-ray CT apparatuses 3 described above are arranged, scanning centers (passing points of the central axes of the CT scanner on a sliced face) may be regarded virtually as isocenters of the apparatuses. In addition, in case X-ray simulators are arranged, center points of rotation radii of the beams, which pass through the center points of irradiation visual fields, may be regarded virtually as isocenters of the apparatuses. Further, when the bed 5 is directed to respective medical apparatuses, a virtual isocenter of the bed 5 is set to coincide with isocenters of respective medical apparatuses. A slight displacement in location of the isocenters may be allowed since reproducibility of medical treatments is not disturbed if an amount of the displacement is always small.

As the medical apparatuses U1, U2, . . . , Un, the linear accelerator 1, the X-ray CT apparatus 3, and the X-ray positioning apparatus may be typically utilized. However, the medical apparatuses are not limited to these apparatuses. Other medical apparatuses and other imaging apparatuses such as MRI, SPECT, etc. may be used. In addition, the medical apparatuses such as the X-ray simulator, the light projector, the operation bed, etc. may be used. These can be applied similarly to the first embodiment.

Finally, a concrete configuration of the medical bed system according to the embodiment of the present invention will be explained.

Figure 11:
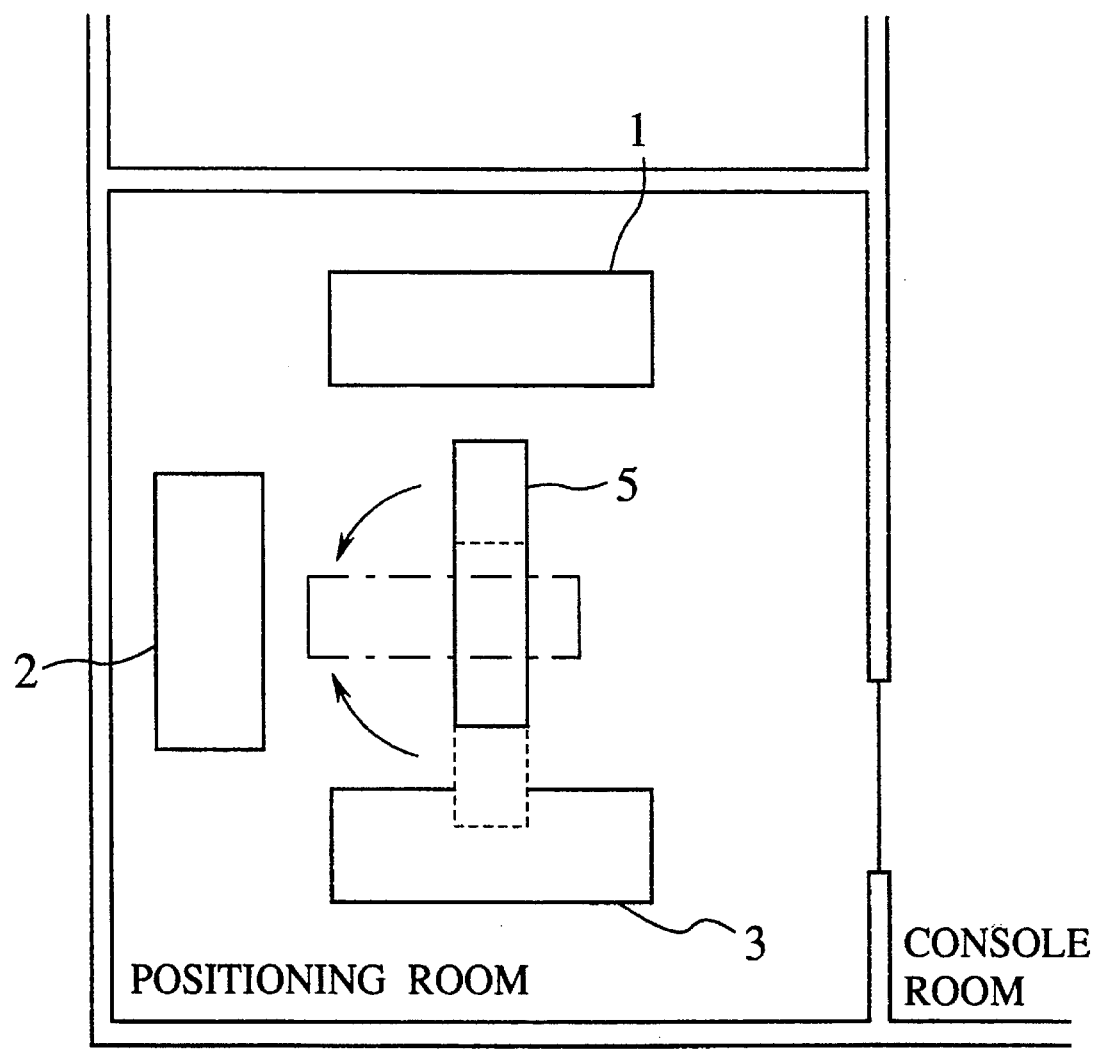
FIG. 11 is a plan view showing a layout of a medical bed system wherein one bed is shared with a therapy positioning apparatus, a linear accelerator, and an X-ray CT apparatus arranged in the same room.
Figure 12A:
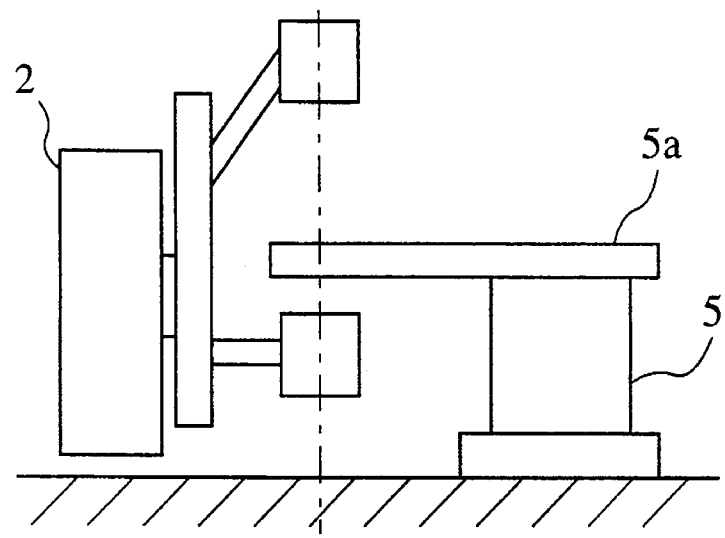
FIGS. 12A to 12C are side views each showing a location relationship between respective medical apparatus and the bed.
Figure 12B:
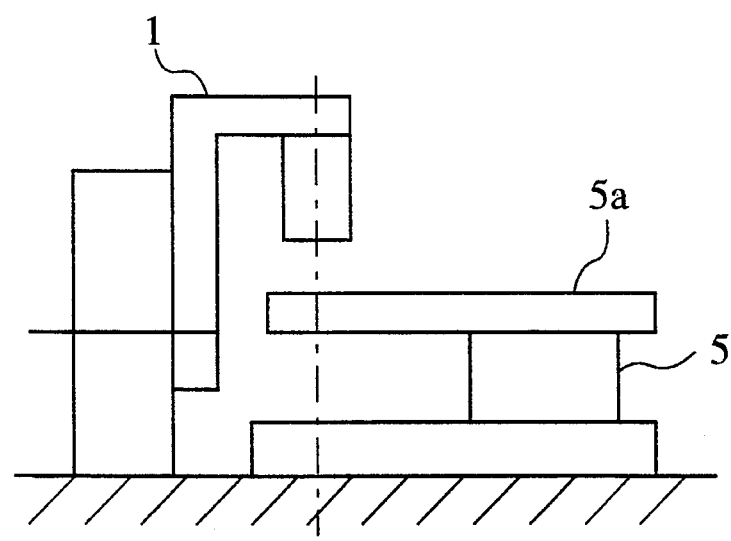
Figure 12C:
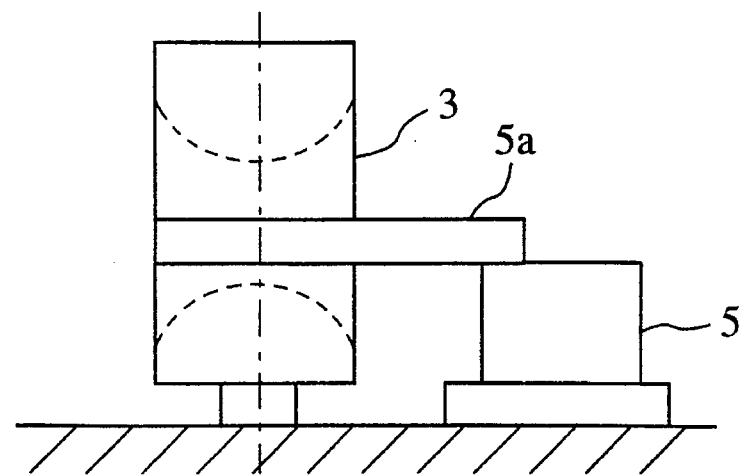

FIG. 11 is a plan view showing a layout of a medical bed system wherein one bed is shared with a therapy positioning apparatus, a linear accelerator, and an X-ray CT apparatus arranged in tile same room. Respective apparatuses are arranged in one positioning room. An operator can operate respective apparatuses by operating a console from an adjacent console room. FIG. 12A is a side view showing a location relationship between the therapy positioning apparatus 2 and the bed 5 in case the therapy positioning apparatus 2 is used. FIG. 12B is a side view showing a location relationship between the linear accelerator 1 and the bed 5 in case the linear accelerator 1 is utilized. FIG. 12C is a side view showing a location relationship between the X-ray CT apparatus 3 and the bed 5 in case the X-ray CT apparatus 3 is utilized. For this reason, respective apparatus of the therapy positioning apparatus 2, the linear accelerator 1, and the X-ray CT apparatus 3 may be respectively operated in the same manner as if each of the apparatuses has own customized bed.

What is claimed is:

1. A medical bed system comprising:

a bed on which a subject lies;

a plurality of medical apparatuses sharing said bed;

means for rotating said bed horizontally around a predetermined central axis so as to position said bed on a predetermined location of respective medical apparatuses; and engaging means for engaging said bed with each of said plurality of medical apparatuses.

2. A medical bed system according to claim 1, wherein said rotating means includes a turn table to be rotated around a predetermined central axis, and a swing arm rotatably mounted on an axis of said turn table.

3. A medical bed system according to claim 1, wherein said rotating means includes a swing arm to be rotated around a predetermined central axis and a turn table rotatably mounted on said swing arm, and each of said plurality of medical apparatuses is arranged such that respective isocenters of said plurality of medical apparatuses are put on a locus of a central axis of said turn table.

4. A medical bed system according to claim 1, wherein said engaging means includes a hook mechanism or a plate and a member to be inserted into said hook mechanism or said plate, which are formed on said medical apparatuses or said bed.

5. A medical bed system according to claim 1, wherein one of said medical apparatus is a linear accelerator.

6. A medical bed system according to claim 1, wherein one of said medical apparatus is a X-ray CT apparatus.

7. A medical bed system according to claim 1, wherein one of said medical apparatus is a therapy positioning apparatus.

8. A medical bed system comprising:

a bed on which a subject lies;

a plurality of medical apparatuses sharing said bed; wherein each of said plurality of medical apparatuses generates a respective bed operation control signal or operating said bed to fit a respective medical apparatus, and supplies said respective bed operation control signal to said bed when it occupies said bed, and said bed controls its operation based on said respective bed operation control signal supplied from said plurality of medical apparatuses.

9. A medical bed system according to claim 8, further comprising:

engaging means for engaging said bed with each of said plurality of medical apparatuses, wherein each of said plurality of medical apparatuses supplies said respective bed operation control signal to said bed when it is engaged with said bed by said engaging means.

10. A medical bed system according to claim 9, wherein each of said plurality of medical apparatuses includes means for detecting own engagement with said bed, and said bed includes means for switching signal lines such that, in response to an output signal of said detecting means, said bed operation control signal is input into said bed from corresponding one of said plurality of medical apparatuses.

11. A medical bed system according to claim 10, wherein said engaging means includes a hook mechanism or a plate and a member to be inserted into said hook mechanism or said plate, which are formed on said medical apparatuses or said bed, and said detecting means includes a microswitch.

12. A medical bed system according to claim 11, wherein said engaging means includes a pair of contact members to which signal lines for supplying said bed operation control signal are connected, and, when said bed is engaged with corresponding one of said plurality of medical apparatuses, both of said pair of contact members are contacted so as to supply said bed operation control signal from the corresponding one of said plurality of medical apparatuses to said bed.

* * * * *